(12) United States Patent
Nottet

(10) Patent No.: US 6,387,959 B1
(45) Date of Patent: May 14, 2002

(54) ANTIVIRAL THERAPY

(75) Inventor: Johannes Servatius Leonardus Maria Nottet, Amsterdam (NL)

(73) Assignees: Universiteit Utrecht; Universitair Medisch Centrum Utrecht, both of Utrecht (NL)

( * ) Notice: Subject to any disclaimer, the term of this patent is extended or adjusted under 35 U.S.C. 154(b) by 0 days.

(21) Appl. No.: 09/608,716

(22) Filed: Jun. 30, 2000

Related U.S. Application Data

(60) Provisional application No. 60/142,297, filed on Jul. 2, 1999.

(51) Int. Cl.[7] .................. A61K 31/10; A61K 31/185; A61K 31/21; A61K 31/235
(52) U.S. Cl. .................. 514/713; 514/576; 514/506; 514/544
(58) Field of Search ............... 514/713, 576, 514/506, 544

(56) References Cited

U.S. PATENT DOCUMENTS 5,973,191 A * 10/1999 Marnett et al. ............. 560/142

OTHER PUBLICATIONS

Kalgutkar et al., Science, (1998), 280(5367), 1268–1270.*

* cited by examiner

Primary Examiner—Minna Moezie
Assistant Examiner—S. Jiang
(74) Attorney, Agent, or Firm—TraskBritt

(57) ABSTRACT

The invention relates to the field of antiviral agents, and more specifically to antiviral therapy. The invention provides use of at least one compound or mixture of compounds of the general formula

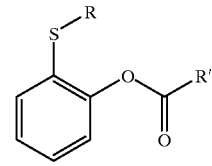

or a functional equivalent or pharmaceutically acceptable salt, ester or hydrate thereof for the treatment of a viral infection.

7 Claims, 7 Drawing Sheets

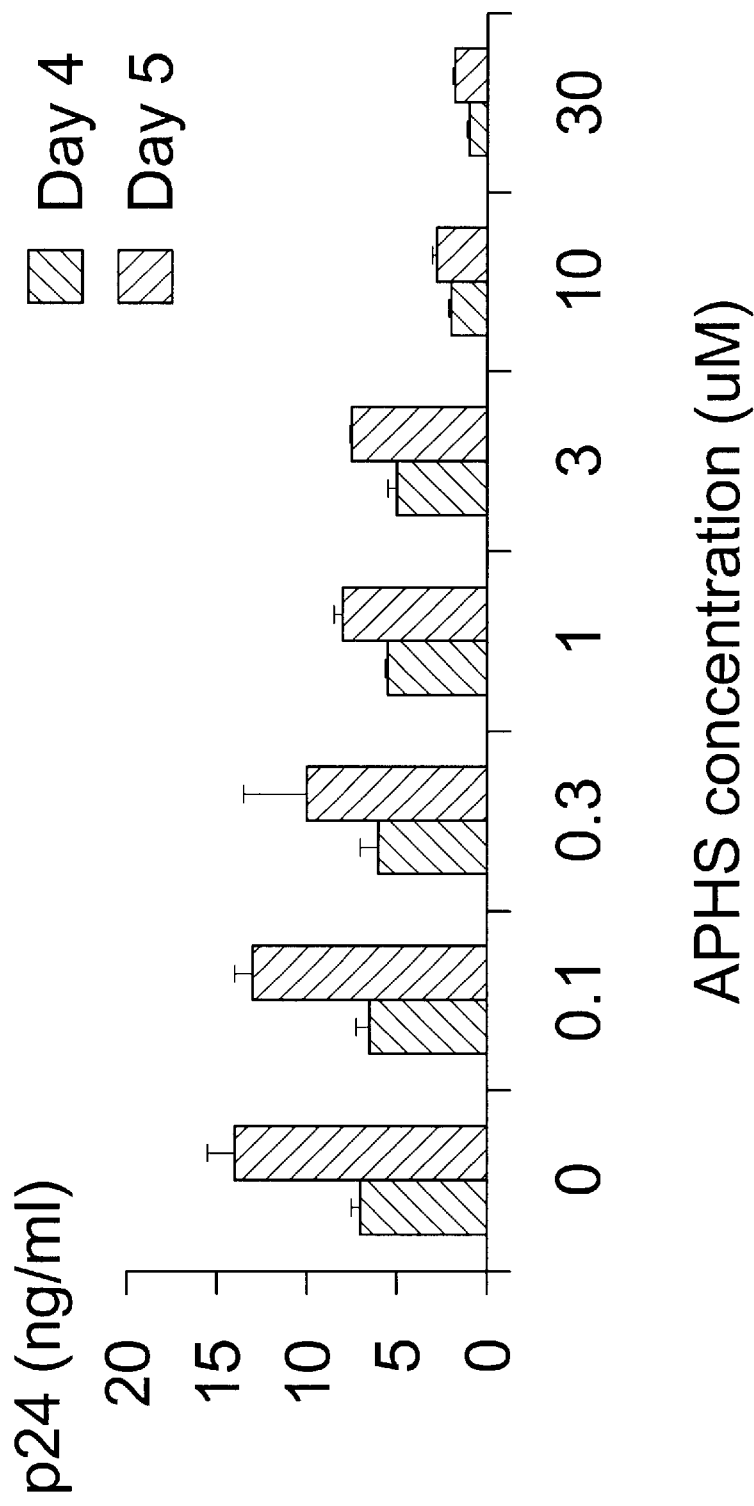

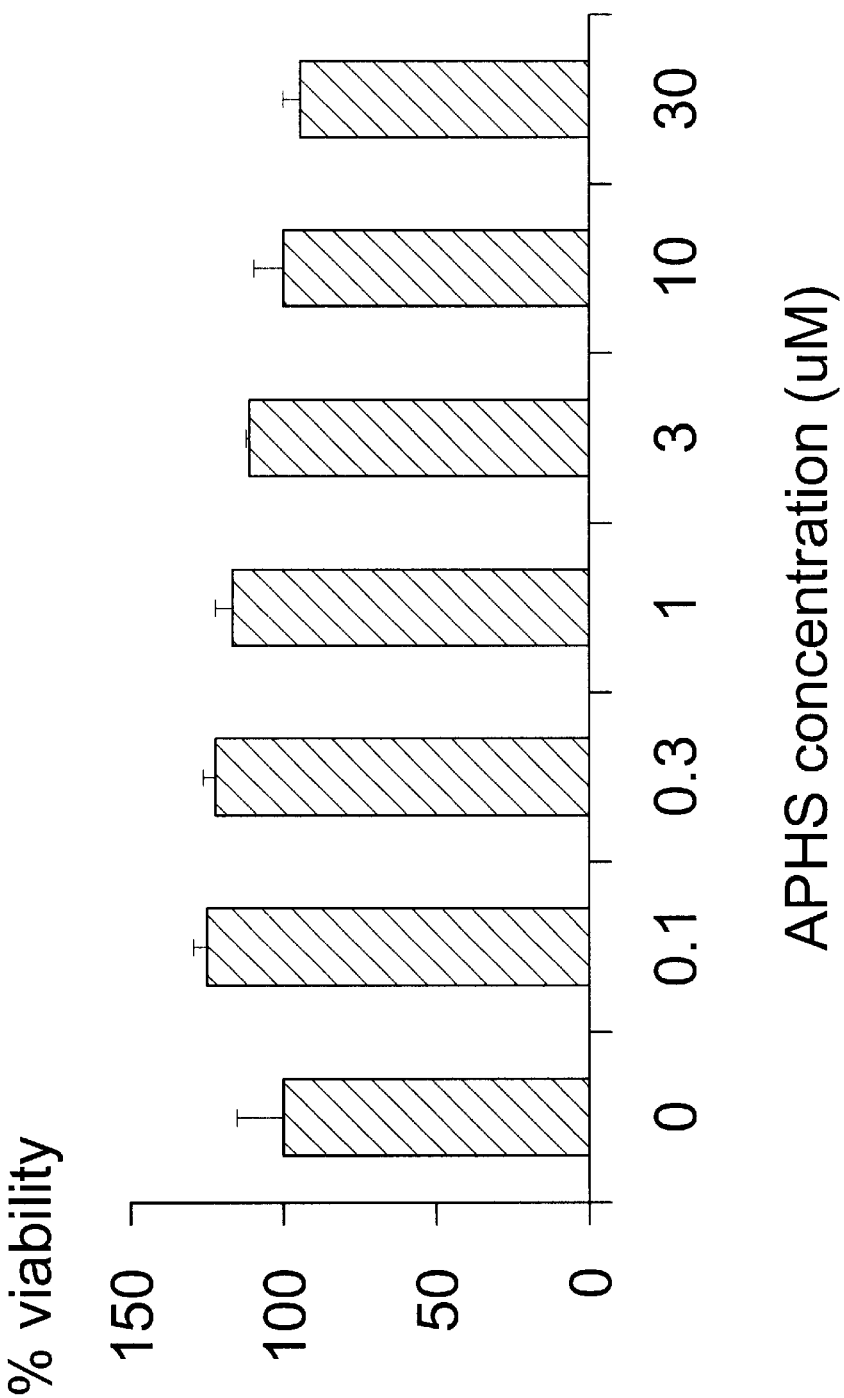

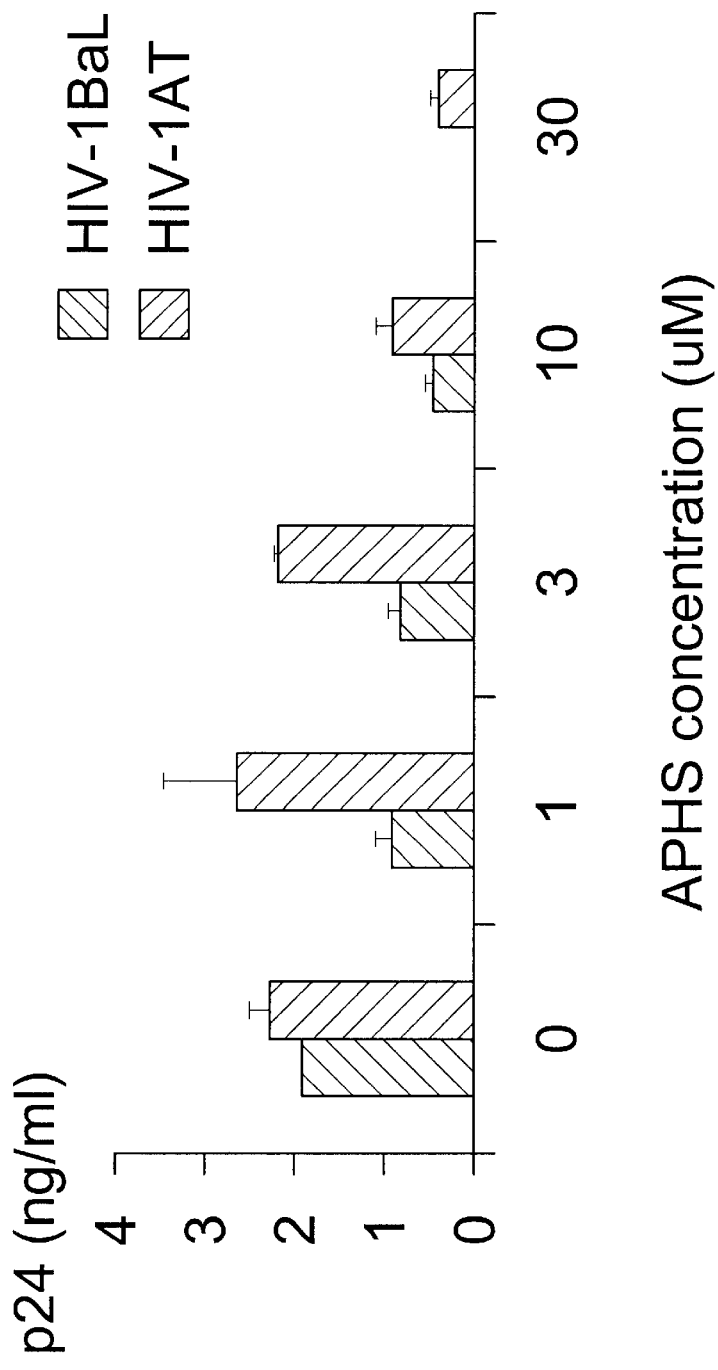

ANTIVIRAL THERAPY

Under the provisions of 35 U.S.C § 119(e), priority is claimed from U.S. Provisional Patent Application Serial No. 60/142,297 filed Jul. 2, 1999.

TECHNICAL FIELD

The invention relates to the field of antiviral agents, and more specifically to antiviral therapy.

BACKGROUND

One of the great paradoxes of medicine is that the simplest of organisms are the most difficult to control. While great progress has been made in controlling more complex organisms, with hundreds of different antibacterial pharmaceutical compositions or antibiotics, there are very few pharmaceutical compositions intended or adapted for antiviral therapy that are of proven effectiveness. The major drawback in developing antiviral agents has been an inability to distinguish viral replicative mechanisms from host replicative processes. Nevertheless, progress has been made over the past two decades in discovering molecules necessary for virus replication, in characterising them mechanistically, and in developing antiviral agents to inhibit them (for review see Hirsch et al., In: Fields Virology, Chapter 15, Lippincot-Raven Publishers, 1996). Well known antiviral agents include amantadine, rimandatine and other anti-influenza agents, acyclovir, gangcyclovir and related agents, foscarnet and other anti-herpesvirus agents, ribavirine and various antiretroviral agents as discussed below.

Progress and understanding in the field of antiretroviral therapy in the past 3 years has been dramatic (for review see Hammer and Yeni. AIDS, 12: S181–S188, 1998). Progress has been fuelled by three major advances. First, increasing knowledge of disease pathogenesis has provided underpinnings for current therapeutic rationale. The proliferative nature of the viral replicative process ($10^{10}$ virions produced and destroyed each day), the rapid viral turnover (virion plasma half-life of 6 h or less), and the recognition of second and third phases of viral decay under the influence of potent antiretroviral therapy resulting from the presence of longer-lived cell reservoirs has guided the current principles of antiretroviral therapy. The second advance has been the widening array of therapeutic choices represented by the increasing numbers of agents available to patients and clinicians. Finally, the third advance is the availability of increasingly sophisticated patient monitoring techniques, such as viral load determinations that simultaneously provide the tools for dissecting HIV disease pathogenesis and monitoring the effects of treatment in affected individuals. Taken together, these developments have led to the generally accepted principle that potent combination regimens (also called highly active antiviral therapy or HAART) designed to drive and maintain plasma HIV-RNA concentration below the limits of detection of currently available assays are the treatments of choice.

However, a number of practical limitations to this idealised approach have increasingly been recognised. These include: the variability of initial virologic response according to the disease stage, particularly the high rate of failure in those with advanced HIV infection; the challenge of patient adherence to complex regimens; drug failure and the threat of multidrug resistance; the lack of predictably effective salvage therapies; the emergence of longer-term toxicities to the protease inhibitor class of compounds; and the sharpening division between populations of the world related to cost and access to effective agents.

In several countries there are 11 agents approved for the treatment of HIV infection and the reasonable expectation is that the total will rise to 15 shortly (Table 1). These agents are either HIV reverse transcriptase inhibitors of the nucleoside, non-nucleoside, and nucleotide subclasses or members of the HIV-protease inhibitor class. Although the simple calculation of the number of two-, three- and four-drug combinations would suggest that the regimen choices for initial and alternative therapies are vast, in reality they are much more limited as a result of cross-resistance, toxicities, tolerance, drug or food interactions and other practical considerations. Although it is true that the options for initial potent, combination regimens are increasing, when one considers the limitations on subsequent regimens conferred by the initial choice, one realises the restricted options for long-term virologic suppression that currently exist.

In areas where drug access is not a problem, the current recommended standard for initial therapy is a potent in vivo protease inhibitor combined with two nucleoside analogs with the first alternative being a non-nucleoside reverse transcriptease inhibitor in combination with two nucleoside analogs. However, the emergence of drug resistance during treatment and its association with treatment failure have been described with nearly all of the antiretroviral agents in use or in development. Therefore, resistance testing might be thought to logically assist with the choice of alternative treatment in the setting of treatment failure and assist with the choice of initial therapy when primary drug resistance is suspected. However, there are many questions that need to be answered before resistance testing (either genotypic or phenotypic) becomes accepted as a routine clinical tool. In what setting and to what extent this technology will improve decision making is not clear and drug resistance is only one of a number of reasons for treatment failure. Resistance testing results are most reflective of the selective pressure of the current drug that might emerge quickly on a new regimen. Further, one cannot always deduce the phenotypic susceptibility of a viral strain from its genotype because of assay sensitivity and resistance mutational interactions. Cross-resistance, particularly to protease inhibitors, may also be a dynamic process in which viruses are "primed" by mutations selected on a previous therapy to develop resistance more quickly when exposed to a new member of the same drug class.

Failure of a particular antiretroviral drug regimen may be defined clinically, immunologically or virologically. Increasingly, for individuals on their initial drug combination a strict definition of failure is being applied. That is, detectable viremia following previous suppression below the detection limit of the assay are being employed. With the advent of plasma HIV-RNA assays with detection limits at the approximate 50 copies/ml range, this has raised the question of whether a confirmed rise above this threshold should trigger a treatment change given the still limited therapeutic armamentarium.

The advances and the limitations of the currently available antiretroviral agents make it clear that new agents and combinations are urgently needed. On the immediate horizon is the promise of widespread availability of four new agents: abacavir (a nucleoside analog reverse transcriptase inhibitor), efavirenz (a non-nucleoside reverse transcriptase inhibitor), adefovir dipivoxil (a nucleotide reverse transcriptase inhibitor), and amprenavir (a protease inhibitor). These agents will carry with them an increasing number of choices for patients and clinicians but are most likely to benefit antiretroviral-naive or minimally drug-experienced individuals only. Their role in "salvage" regimens is currently under investigation but the potential for cross-resistance with the currently approved agents may well limit their effectiveness in this circumstance.

In conclusion, a next wave of drug development is needed that involves new classes of antiviral agents. Other potential anti-viral agents effective against viral targets are needed to broaden the therapeutic possibilities of viral therapy.

SUMMARY OF THE PRESENT INVENTION

The present invention provides use of at least one compound or mixture of compounds of the general formula

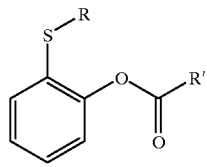

or a functional equivalent or pharmaceutically acceptable salt, ester or hydrate thereof for the production of a pharmaceutical composition for the treatment of a viral infection. Replacements or substitutions of the general formula for example include replacing S with O, Se or Te, and/or additionally substituting the ring with one or more side groups such as R or R'.

Compounds of the general formula are for example known from Arnoldi et al., J. Chem. Soc., Perkin Trans. 1 (1993), 12:1359–1366; from Poirier et al., Sulfur Lett. (1998) 10:167–173; and from Ohtsuka et al., Chem. Pharm. Bull. (1983) 31:443–453. Furthermore, it is known from Kalgutar et al., Science 280:1268–1270, (1998) and WO 98/29382 that compounds of the general formula covalently inactivate cyclo-oxygenase-2 (COX-2) and are selective inhibitors of prostaglandin endoperoxidase-2 and that a pharmaceutical composition including such compound may be useful for providing pain-relief, such as in the prophylaxis or therapeutic treatment of inflammatory responses such as oedema, fever, algesia, neuromuscular pain, headache, cancer pain or arthritic pain.

Surprisingly, however, it has now found that a pharmaceutical composition including the compound is useful in anti-viral therapy. Not wishing to be bound by theory it is herein assumed that a compound of the general formula or a functional equivalent thereof for example inhibits prostaglandin synthesis by COX-2 and/or binds PPAR-g (peroxisome proliferator-activated receptor-g, a member of the nuclear receptor family of transcription factors) or PPAR-g analogues and therewith antagonises activities of transcription factors such as AP-1, STAT and NF-kB, assumedly with the effect that viral functions such as virus transcription and/or viral gene expression are functionally inhibited, as for example can be detected by testing the effect of such compound on viral promotor activity (see e.g. FIG. 1). Alternatively, the effect on viral protein expression is detected by testing viral protein production in cell culture (see e.g. FIGS. 2, 4a and 4b).

BRIEF DESCRIPTION OF THE DRAWINGS

FIG. 2: Peripheral blood mononuclear cells (PBMC) were isolated from heparinized blood from HIV-1-, HIV-2-, and hepatitis B-seronegative donors and obtained on Ficoll-Hypaque density gradients. PBMC were washed twice and monocytes were purified by countercurrent centrifugal elutriation. Cells were >98% monocytes by criteria of cell morphology on May-Grünwald-Giemsa-stained cytosmears and by nonspecific esterase staining using alpha-naphtylacetate as substrate. Monocytes were cultured in suspension at a concentration of $2 \times 10^6$ cells/ml in Teflon flasks in Iscove's modified Dulbeco's medium (IMDM) with 10% heat-inactivated human AB serum negative for anti-HIV antibodies, 10 mg/ml gentamicin, and 10 mg/ml ciprofloxacin. After 7 days of incubation non-adherent monocyte-derived macrophages (MDM) were recovered from the Teflon flasks, washed and infected with HIV-$1_{Ba-L}$ at a multiplicity of infection of 0.02 for two hours. HIV-infected and mock-infected MDM's were washed twice to remove unbound virus and cultured for 4 to 7 days in different concentrations of APHS. After 4 and 5 days of incubation samples of culture supernatant were collected and p24-core antigen production was quantified using the enzyme-linked immunosorbent assay (ELISA) system of John Moore. Concentrations above 0.3 mM APHS inhibit p24 production. 30 mM APHS inhibits HIV-1 replication by 88%.

FIG. 3: Monocyte-derived macrophages (MDM) were obtained like described in legend of FIG. 2. MDM were then washed twice and cultured for 4 to 7 days in different concentrations of APHS. After a 4 days incubation period cellular viability was assessed by MTT cytotoxicity assay where viable cells convert MTT into a colored formazan dye that can be measured spectrophotometrically. None of the tested concentrations of APHS was found to be cytotoxic.

FIGS. 4a–c: Peripheral blood mononuclear cells (PBMC) were isolated from heparinized blood from HIV-1-, HIV-2-, and hepatitis B-seronegative donors and obtained on Ficoll-Hypaque density gradients. Cells were washed twice, stimulated with 5 mg/ml phytohemagglutinin (PHA), and cultured in RPMI-1640 medium supplemented with 5 mM Hepes, 19 mM sodium bicarbonate, 10 mg/mL gentamicin, and 10% heat-inactivated fetal calf serum at a concentration of $2 \times 10^6$ cells/ml. After 3 days of incubation stimulated PBMC were recovered from the flasks and infected for 2 hours with (a) HIV-$1_{AT}$ at a multiplicity of infection of 0.001, (b) HIV-$1_{BaL}$ at a multiplicity of infection of 0.006 and (c) HIV-$1_{BaL}$ or HIV-$1_{AT}$ at a multiplicity of infection of 0.01 or 0.001, respectively. HIV-infected and mock-infected PBMC were washed twice to remove unbound virus and cultured for 4 to 7 days in different concentrations of APHS. After 4 and 5 days of incubation samples of culture supernatant were collected and p24-core antigen production was quantified using the enzyme-linked immunosorbent assay (ELISA) system of John Moore.

Concentrations above 1 mM APHS inhibit HIV-1 production. 30 mM APHS inhibit HIV-$1_{BaL}$ replication by 100%. When infectivity is lower (FIG. 4c), 1 mM APHS inhibit HIV-$1_{BaL}$ production by at least 50%.

Figure 4A:
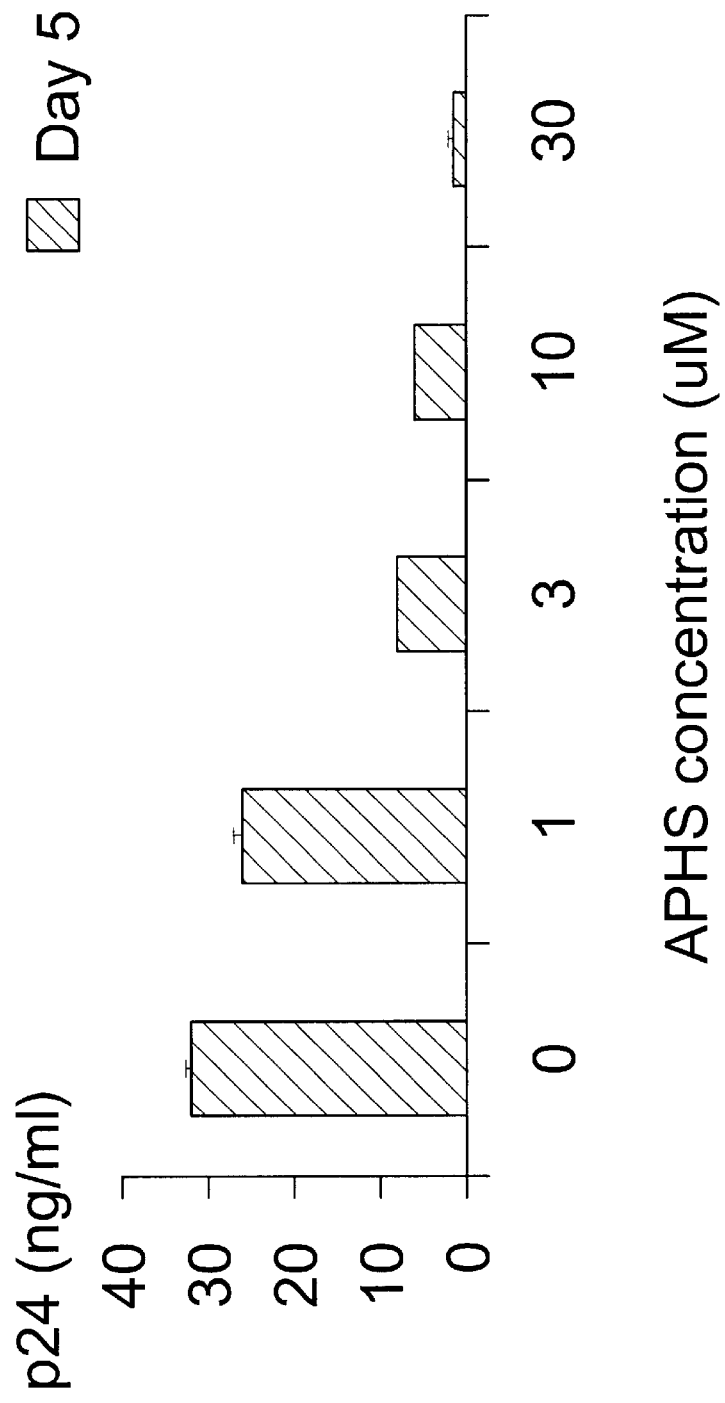
Figure 4B:
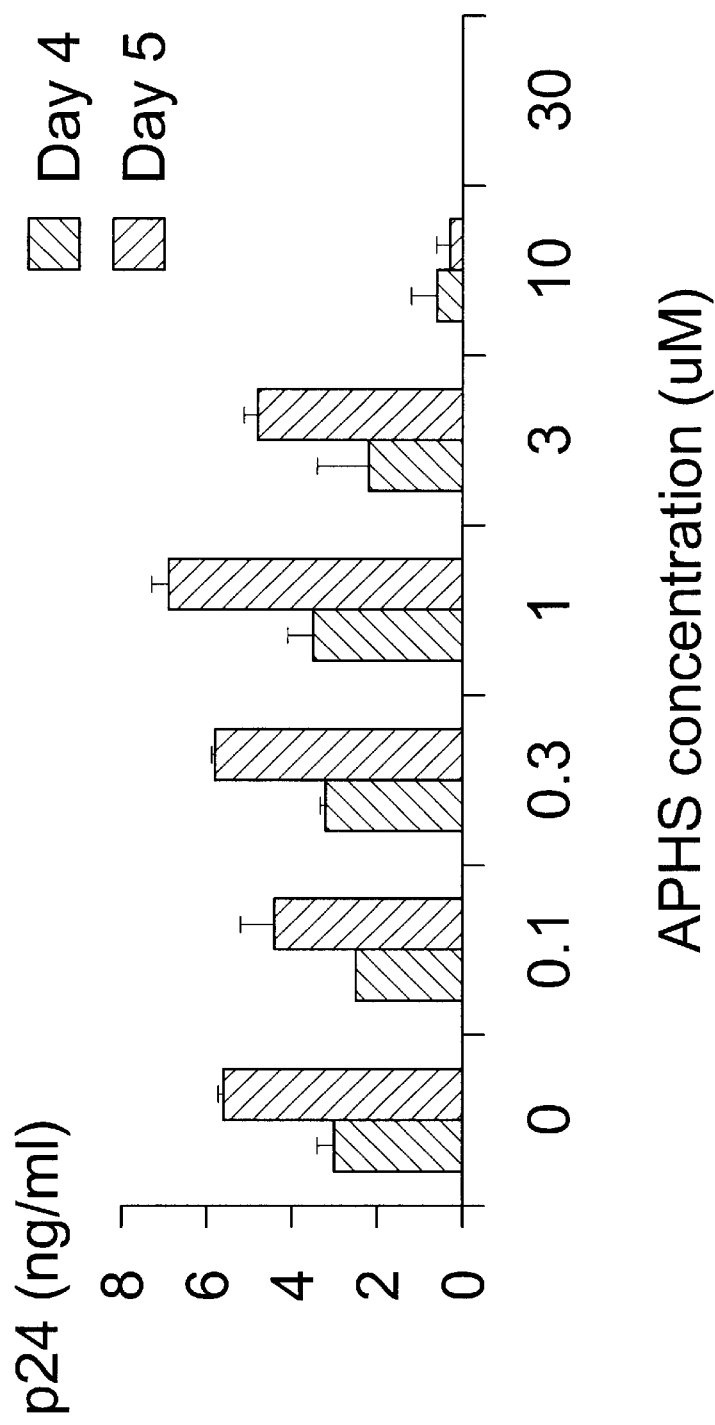
Figure 5:
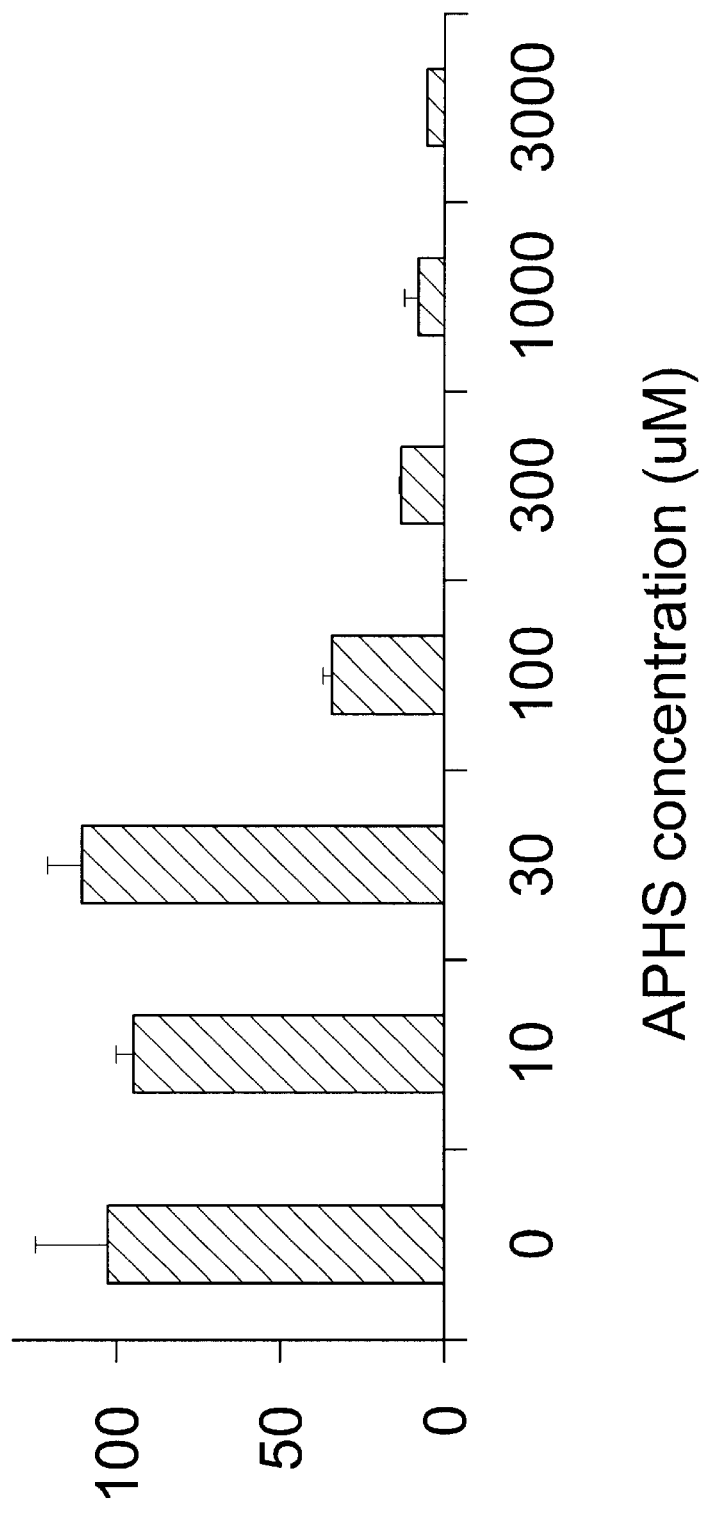

FIG. 5: PBMC were obtained and stimulated as described in legend of FIG. 4. 3 days after incubation PBMC were recovered from the flasks, washed and cultured for 4 to 7 days in different concentrations of APHS. After a 5 days incubation period cellular viability was assessed by WST-1 cytotoxicity assay where viable cells convert WST-1 into a coloured formazan dye that can be measured spectrophotometrically. Concentrations at or above 100 mM were found to reduce viability.

TABLE 1

Antiretroviral agents (approved or in advanced development).

Nucleoside analogue reverse transcriptase inhibitors

Zidovudine (ZDV, AZT)
Didanosine (ddI)
Zalcitabine (ddC)
Stavudine (d4T)
Lamivudine (3TC)
Abacavir (1592U89)

Non-nucleoside reverse transcriptase inhibitors

Nevirapine
Delavirdine
Efavirenz (DMP-266)

Nucleotide analogue reverse transcriptase inhibitors

Adefovir dipivoxil

Protease inhibitors

Saquinavir
Ritonavir
Indinavir
Nelfinavir
Amprenavir (141W94, VX-478)

DETAILED DESCRIPTION OF THE INVENTION

A preferred embodiment provides use according to the invention of a compound of the general formula as discussed above or a pharmaceutically acceptable salt or hydrate thereof wherein R is H, $CF_3$ or a C1–C10, branched or unbranched, substituted or unsubstituted (preferably the substitute is a halogen), saturated or (poly)unsaturated, (cyclo)alkyl, alkene, alkyne, (cyclo)aryl, aryl(cyclo)alkyl, (cyclo)alkylaryl, alkoxyaryl, alkoxyalkene, alkoxyalkyne, enyne, diene, diyne or alkoxyalkyl, preferably selected from the group consisting of H, $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $CH(CH_3)_2$, $C(CH_3)_3$, $CH=C=CH_2$, $(CH_2)_2O(CH_2)_3CH_3$, $CH_2HC=CH$ $(CH_2)_3CH_3$, $CH_2C\equiv C$ $(CH_2)_3CH_3$, $CCH_2C\equiv C$ $(CH_2)_2CH_3$, $CH_2C\equiv C-CH_2CH_3$, $CH_2C\equiv C-CH_3$ AND $CH_2C\equiv CH$ and isomers or homologues thereof; and wherein R' is R, preferably selected from the group consisting of H, $CH_3$, $CF_3$, $CH_2Cl$ and $CH_2Br$.

The present invention also provides a pharmaceutical composition intended and adapted for the treatment of a viral infection (herein also called an antiviral agent) including at least one compound or a mixture of compounds according to the general formula and a pharmaceutically acceptable carrier of diluent. In order to use a compound according to the general formula or a pharmaceutically acceptable salt or hydrate thereof in therapy, it will normally be formulated into a pharmaceutical composition in accordance with standard pharmaceutical practice. This invention, therefore, also relates to a pharmaceutical composition for the treatment of a viral infection including an effective amount of a compound according to the general formula and pharmaceutically acceptable carrier or diluent. A pharmaceutical composition as provided by the invention allows for treatment in a conveniently wide therapeutic window. Toxicity for cells, for example, is evaluated on the level of cell-viability as shown in FIGS. 3 and 5. Similarly, it can be evaluated as shown in FIGS. 2, 4a and 4b where significant anti-viral activity is found.

In a preferred embodiment, the invention provides use according to the invention wherein the viral infection includes a retroviral infection. Such a retroviral infection can for example include a leukemia virus infection, such as caused by bovine leukemia virus or human T-cell-leukemia virus. Other retroviral infections known in the art include ovine lentivirus infections and spumaretrovirus infections. Also, a retroviral infection can include an infection with a recombinant retrovirus which is constructed for use in gene therapy. Preferably, the invention provides use wherein the retroviral infection is caused by a immunodeficiency virus such as human or simian immunodeficiency virus (HIV or SIV). As an example, HIV-1 infection of T-cells and macrophages is mediated by CD4 and the recently discovered chemokine receptors such as CCR-5, CXCR-4, CCR2b and CCR-3. After binding of HIV-1 gp120 to these receptors fusion of viral and cellular membranes occurs resulting in the release of the viral preintegration complex into the cytoplasm. Subsequently the matrix domain of the HIV-1 gag protein mediates the translocation of the HIV-1 preintegration complex to the nucleus. Formation of HIV-1 DNA occurs already within the preintegration complex and can even be formed within the intact virion itself. Complete HIV-1 DNA consists in several forms but, however, a crucial step in infection is the integration of viral DNA into the chromosomal host cell DNA. At this stage in the viral life cycle the cell is infected for life. Current anti-HIV compounds are directed against various stages in the HIV-1 life cycle. For instance, the nucleoside and non-nucleoside analogs are directed against reverse transcriptase, the enzyme that converts the viral RNA into DNA. In such a way virions released by HIV-infected cells are not infectious for other target cells, unless mutations in the reverse transcriptase occur that confer resistance to these classes of anti-HIV drugs. Another class of anti-HIV compounds that is part of all new triple anti-HIV therapy treatment regimens are the protease inhibitors. These compounds likely prevent the formation of complete virions by HIV-infected cells and thus are intended to prevent the spread of HIV-1 to new target cells. For example, FIGS. 2, 4a and 4b show that a pharmaceutical composition including a compound according to the general formula, as provided by the invention, allow for a novel antiviral therapy to be provided by the invention.

Furthermore, the invention provides use wherein the treatment additionally includes treatment with another pharmaceutical composition. For example, combinatorial therapy to treat virus infections, as is often the case when HIV-infected individuals are treated, is now provided wherein the other pharmaceutical composition at least includes an antiviral agent, such as amantadine and rimandatine or other anti-influenza agents such as acyclovir, gangcyclovir or related agent, foscarnet or other anti-herpesvirus agent, ribavirine or an antiretroviral agent such as for example known from table 1, or an antiviral agent as provided by the invention. Combination therapies include an anti-viral agent according to the invention, and additionally include more than one additional anti-viral agent, such as the combinations of the anti-viral agent as provided by the invention with nucleoside analogue reverse transcriptase inhibitors and/or with non-nucleoside reverse transcriptase inhibitors and/or with nucleotide analogue reverse transcriptase inhibitors and/or with protease inhibitors.

Additionally, the invention provides use according to the invention wherein the treatment additionally includes treatment of inflammatory responses, such as oedema, fever, algesia, neuromuscular pain, headache, cancer or arthritic pain; viral-infection-related or -associated dementia's, or other bodily ailments.

Furthermore, the invention provides a pharmaceutical composition intended and adapted for anti-viral therapy including a compound of the general formula or functional equivalent thereof. Preferably, the pharmaceutical composition intended and adapted for anti-viral therapy includes a compound of the general formula wherein R or R' are as defined above. Preferably, an anti-viral agent as provided by the invention includes 2 acetoxythioanisole, 2-(trifluoromethylacetoxy)thioanisole, 2-(chloroace-toxy)thioanisole, 2-(bromoacetoxy)thioanisole, 2-acetoxyphenylbenzyl sulphide, 2-acetoxyphenzyl-2-phenylethyl sulphide, 2-acetoxyphenylethyl sulphide, 2-acetoxyphenylpropyl sulphide, 2-acetoxyphenyl-butyl sulphide, 2-acetoxyphenylpentyl sulphide, 2-acetoxy-phenylhexyl sulphide, 2-acetoxyphenylheptyl sulphide, 2-acetoxyphenyl-2-butoxyethyl sulphide, 2-acetoxyphenyl-2-trans-heptenyl sulphide, 2-acetoxyphenylhept-2-ynyl sulphide, 2-acetoxyphenylbut-2-ynyl sulphide, 2-acetoxyphenylprop-2-ynyl sulphide, or o-(acetoxyphenyl)hept-2-ynyl sulphide (APHS), or a pharmaceutically acceptable salt or hydrate thereof. Suitable pharmaceutically acceptable salts are well known to those skilled in the art and include basic salts of inorganic and organic acids, such as hydrochloric acid, hydrobromic acid, sulphonic acid, phosphoric acid, methane sulphonic acid, ethane sulphonic acid, acetic acid, malic acid, tartaric acid, maleic acid, benzoic acid, salicylic acid, phenylacetic acid and mandelic acid. In addition, pharmaceutically acceptable salts of a compound according to the general formula may also be formed with a pharmaceutically acceptable cation, for instance, if a substituent group includes a carboxy moiety. Suitable pharmaceutically acceptable cations are well known in the art and include alkaline, alkaline earth ammonium and quaternary ammonium cations.

In addition, the invention provides a pharmaceutical composition intended and adapted for anti-viral therapy including a compound of the general formula or functional equivalent thereof the composition at least combined, preferably mixed with a pharmaceutical composition that at least includes another antiviral agent, such as for example amantadine, rimandatine or other anti-influenza agents, acyclovir, gangcyclovir or related agents, foscarnet or other anti-herpesvirus agent, ribavirine or a antiretroviral agent such as for example known from table 1, or an antiviral agent as provided by the invention. Such a composition as provided by the invention can advantageously be used in combinatorial anti-viral therapy.

The invention also provides a method to treat a viral infection of an animal including administering to the animal an anti-viral agent according to the invention or subjecting the animal to treatment with an anti-viral agent according the invention. An anti-viral agent including a compound according to the general formula, a pharmaceutically acceptable salt thereof and a pharmaceutical composition incorporating such, may be conveniently administered by any of the routes conventionally used for drug administration, e.g., orally, topically, parenterally or by inhalation. A compound according to the general formula may be administered in conventional dosage forms prepared by combining a compound according to the general formula with a standard pharmaceutical carrier according to conventional procedures.

An anti-viral agent that includes a compound according to the general formula may be administered parenterally, i.e., by intravenous, intramuscular, subcutaneous, intranasal, intrarectal, intravaginal or intraperitoneal administration. Subcutaneous and intramuscular forms of parenteral administration are generally preferred. Appropriate dosage forms and dosage regimes for such administration may be prepared by conventional techniques or arrived at by dose finding studies. Compounds may also be administered by inhalation e.g., intranasal and oral inhalation administration. Appropriate dosage forms or regimes for such administration, such as aerosol formulation or metered dose inhaler may be prepared by conventional techniques well known to those having ordinary skill in this art.

An anti-viral agent of the present invention may also be administered in combination with a known, second therapeutically active compound or composition. These procedures may involve mixing, granulating, compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variables. The carrier(s) must be "acceptable" in the sense of being compatible with the other ingredients of the formulation and not deleterious to the recipient thereof.

In particular, the invention provides a method to treat a viral infection that includes administering an anti-viral agent to the animal according to the invention or subjecting the animal to treatment with the agent wherein the viral infection is a retroviral infection. In particular, the invention provides a method to treat a viral infection wherein the animal is human. In the case of viral infections it is considered especially advantageous to combine treatment of a viral infection with an anti-viral agent according to the invention with treatment with at least one other anti-viral agent, especially with an anti-viral agent as can be found in table 1, thereby greatly enhancing the possible number of combinations that can be used to for example treat patients with retroviral infections such as AIDS or AIDS-related infections, thereby enhancing therapeutic possibilities for combinatorial or highly active antiviral therapy (HAART). The invention is further explained with use of the following EXPERIMENTAL portion.

EXPERIMENTAL

1. Materials and Methods Related to Cells 1.a. Isolation and Culture of Peripheral Blood Mononuclear Cells Peripheral blood mononuclear cell (PBMC) fractions are isolated from heparinised blood from HIV-1-, HIV-2- and hepatitis B- seronegative donors (Blood-bank, Utrecht, the Netherlands) by Ficoll-Isopaque gradient separation. Cells are washed twice, stimulated with 4 mg/ml phytohemagglutinin (PHA), and cultured in RPMI-1640 medium supplemented with 5 mM Hepes, 19 mM sodium bicarbonate, 10 mg/ml gentamicin, and 10% heat-inactivated fetal calf serum at a concentration of $1 \times 10^6$ cells/ml.

1.b. Isolation and Culture of Monocyte-Derived Macrophages (MDM)

PBMC are isolated from heparinized blood from HIV-1-, HIV-2-, and hepatitis B-seronegative donors and obtained on Ficoll-Hypaque density gradients. Cells are washed twice and monocytes are purified by countercurrent centrifugal elutriation. Cells are >98% monocytes by criteria of cell morphology on May-Grünwald-Giemsa-stained cytosmears and by nonspecific esterase staining using alpha-naphtylacetate (Sigma Chemical Co., St. Louis, Mo.) as substrate. Monocytes are cultured in suspension at a concentration of $2 \times 10^6$ cells/ml in Teflon flasks (Nalgene, Rochester, ANY.) in Iscove's modified Dulbeco's medium (IMDM) with 10% heat-inactivated human AB serum negative for anti-HIV antibodies, 10 mg/ml gentamicin, and 10 mg/ml ciprofloxacin (Sigma) for 7 days.

1.c. Peripheral Blood Lymphocyte Isolation

PBMC fractions are isolated from heparinized blood from HIV-1-, HIV-2- and hepatitis B- seronegative donors (Blood-bank, Utrecht, the Netherlands) by Ficoll-Isopaque gradient separation. After the cells are washed twice monocytes are allowed to adhere on fibronectin-coated flasks before the PBL fraction is harvested. The PBL fractions collected are of >85% purity as determined by May-Grünwald-Giemsa-staining. Isolated PBL are stimulated to proliferate for 3 days with 4 mg/ml phytohemagglutinin (PHA; Sigma). PBL are cultured in RPMI-1640 (Life Technologies Ltd.) medium supplemented with 10% heat inactivated fetal calf serum (LifeTechnologies Ltd.) and 10 mg/ml gentamicin (Life Technologies Ltd.). After PHA stimulation the cells are cultured in medium containing 10 U/ml human recombinant IL-2 (Boehringer) until use. Viability is >95% at the point of the initiation of the experiment as determined by trypan-blue exclusion.

1.d. Determination of Cell Viability Using the MTT Assay

Cell viability is assessed by the MTT assay. In short, cells are incubated with MTT 3-(4,5-dimethylthiazol-2-yl)-2,5-diphenyltetrazollumbromide (Sigma) for 2 hours at 37° C. During this time viable cells convert MTT into water forming insoluble formazan dyes. Afterwards crystals are solubilised with a solution containing isopropanol. The OD of the supernatant is measured at 550 nm.

1.e. Determination of Cell Viability Using the WST-1 Assay

Cell viability is assessed with WST-1 assay. Cells are incubated with the tetrazolium salt WST-1 (4-[3-(4-lodophenyl)-2-(4-nitrophenyl)-2H-5-tetrazolio]-1,3-benzene disulfonate) for 2 hours at 37° C. During this time viable cells convert WST-1 into water soluble formazan dyes. The OD of the supernatant is measured at 550 nm.

2. Materials and Methods Related to Virus Infection 2.a. Preparation of Viral Stocks HIV-1 strain Ba-L is grown to high titer in MDM. The 50% tissue culture infectious dose (TCID50) of the virus stock is determined by endpoint dilution with serial fourfold dilutions in a 96-well microtiter plate on MDM. HIV-1 strain AT is grown to high titer in PHA-stimulated PBMC. The TCID50 of the virus stock is determined by endpoint dilution with serial fourfold dilutions in a 96-well microtiter plate on PBMC.

2.b. HIV-1 Infection of Cells (as Determined by ELISA)

MDM, and PBMC, were incubated with HIV at a multiplicity of infection of 0.02, and 0.006 or 0.001, respectively. After two hours cells are washed to remove unbound virus and cultured for 4 to 7 days in different concentrations of the drug under investigation. On day 4, 5 and 7, 0.01 ml of supernatant is removed from the culture and virus in culture supernatant is inactivated in a final concentration of 0.05% empigen (Calbiochem-Novabiochem Co., La Jolla, Calif.). The presence of HIV-1 in the inactivated supernatant is monitored by checking for the p24-core antigen using the enzyme-linked immunosorbent assay (ELISA) system of John Moore.

3. Detection Assays to Test for the Action of the Drugs in the HIV Life Cycle 3.a. HIV-1 Infection of Cells Transfected with Different Chemokine Receptors to Study the Effect on HIV-1 Entry into the Cell The cell line HOS-CD4 and the cell lines that are derived from HOS-CD4, namely HOS-CD4-CCR2b, HOS-CD4-CCR3, HOS-CD4-CCR5 and HOS-CD4-CXCR4 are obtainable through the AIDS Research and Reference Reagent Program. These cell lines express the chemokine receptors that are used by the different HIV-1 strains and are used for investigation of the effect of compounds of above identified general formula and related compounds on their antiviral effect on the different HIV-1 strains and on modulation of these chemokine receptors.

In short, cells are infected with an appropriate viral strain and the anti-viral effect of the compounds is measured by HIV p24 antigen ELISA. Furthermore, the cells are incubated with a monoclonal antibody directed against the chemokine receptor studied. Then the cells will be washed twice with phosphate-buffered saline and analyzed on a FACStar flow cytometer (Beckton Dickinson and Co., Mountain View, Calif.).

3.b. RNA PCR detection of HIV-1 Infection to Study the Effect on the Transcriptional Level The HIV-infected cells are lysed in 1 ml TRIzol (Life Technologies Gaithersburg, Md.) and RNA is isolated according to the manufacturer's guidelines. Total RNA is dissolved in diethylpyrocarbonate (DEPC)-treated water and 1 mg of RNA is used for the synthesis of complementary DNA. The RNA is previously heated for 5 minutes at 70° C., chilled on ice and added to a mixture containing 1× reverse transcriptase (RT) buffer (Promega, Madison, Wis.), 200 U of reverse transcriptase, 0.1 M dithiothreitol (DTT, Gibco, Grand Island, N.Y.), 2.5 mM deoxynucleotidetriphosphate (dNTP's, Boehringer Mannheim, Indianapolis, Ind.), 80 U random hexamer oligonucleotides (Boehringer Mannheim) and 10 U RNAsin (Promega). The complete mixture is now incubated for 60 minutes at 37° C. and then heated for 5 minutes at 90° C. The final reaction volume is diluted 1:8 by adding distilled water. Amplification of the cDNA is accomplished using one primer biotinylated on the 5' terminal nucleotide to facilitate later capture using streptavidin. To the PCR reaction mixture the following components are added: 0.25 mM dNTP mix (Boehringer Mannheim), 1×PCR buffer (50 mM KCl, 10 mM Tris-HCl, 1.5 mM $MgCl_2$; Promega), 0.2 mM of the biotinylated HIV-1 tat/rev sense primer 5' GGC TTA GGC ATC TCC TAT GGC 3' or GAPDH sense primer 5' CCA TGG AGA AGG CTG GGG 3' and the antisense HIV-1 tat/rev primer 5' TGT CGG GTC CCC TCG TTG CTG G 3' or the antisense GAPDH primer 5' CAA AGT TGT CAT GGA TGA CC 3', 5 ml CDNA and 1 U Taq polymerase (Promega). Denaturation, annealing, and elongation temperatures for PCR are 94° C., 60° C., and 72° C. for 1, 1, and 2 min each, using a DNA thermal cycler (Perkin-Elmer, Norwalk, Conn.). Negative controls are included in each assay to confirm that none of the reagents are contaminated with CDNA or previous PCR products. PCR is also performed on RNA samples to exclude genomic DNA contamination. To confirm single band product positive reactions are subjected to 40 cycles amplification and electrophoresis followed by ethidium bromide staining. Then, for semi-quantification every primer pair is tested at different cycle numbers to determine the linear range. GAPDH mRNA levels are high and 25 cycles is enough to measure the PCR product in its linear range, whereas HIV-1 tat/rev cDNA is subjected to 38 cycles to be in the linear range, when needed. Aliquots of 5 ml of the biotinylated PCR product are semi-quantitatively analyzed using a fluorescent digoxigenin detection ELISA kit (Boehringer Mannheim) according to manufacturer's protocol. In short, the biotinylated strand of denatured PCR product is captured by immobilized streptavidin. Then, a digoxigenin labeled probe (the probe for HIV-1 tat/rev is 5' CTT TGA TAG AGA AAC TTG ATG AGT CTG 3' and the probe for GAPDH is 5' CTG CAC CAC CAA CTG CTT AGC 3') is added followed by an alkaline phosphatase labeled antibody against digoxigenin. After addition of the substrate fluorescence is measured in relative fluorescence units (RFU) in a fluorescence multi-well plate reader (Perseptive biosystems, Framingham, Mass.) at excitation 450 nm/emission 550 nm. All data are normalized against GAPDH mRNA levels, which is used as an internal standard.

3.c. DNA PCR Detection of HIV-1 Infection to Study the Effect on the Earliest Processes of Proviral DNA Formation Trizol reagent is used for DNA isolation according to the manufacturer's protocol. In short, DNA and RNA of cell samples in trizol are isolated by chloroform. DNA is precipitated from the lower chloroform phase by 100% ethanol and the sedimented DNA is washed twice in 0.1 M sodium citrate in 10% ethanol. The pellet is reconstituted in water and checked for purity by measuring the OD260/280 ratio. The earliest processes of proviral DNA formation is analyzed by checking for the formation of the HIV R/U5 product indicating that the process of reverse transcription has taken place. The R/U5 primer pair flanks sequences within the first region of viral DNA synthesized as a result of reverse transcription, this first fragment of DNA is referred to as strong-stop minus DNA. The primer set which we use detects the early steps in reverse transcription and determines whether any viral DNA is synthesized in infected cells in the presence of APHS and derivates. The method and conditions of the PCR reaction are essentially the same as described in section 3.a. The R/U5 primer pairs (Zack et al, 1990): sense 5'-GGCTAACTAGGGAACCCACTG-3' and antisense 5'-TGTGTGCCCGTCTGTTGTGTG-3' (5' end biotinylated) result in a 132bp fragment. The digoxigenin-labeled probe 5'-TGTGTGCCCGTCTGTTGTGTG-3' is used to quantify the fragment. PCR amplification conditions are denaturation at 94° C. for 5 min followed by 38 cycles of denaturation at 94° C. for 1 min, annealing at 60° C. for 1 min and extension at 72° C. for 2 mins. The DNA product is finally extended at 72° C. for 10 mins. 5 ml of the amplified product is quantified using the digoxigenin-labeled probe, by means of a DIG-detection ELISA (Boehringer-Mannheim, Mannheim, Germany).

Figure 1:
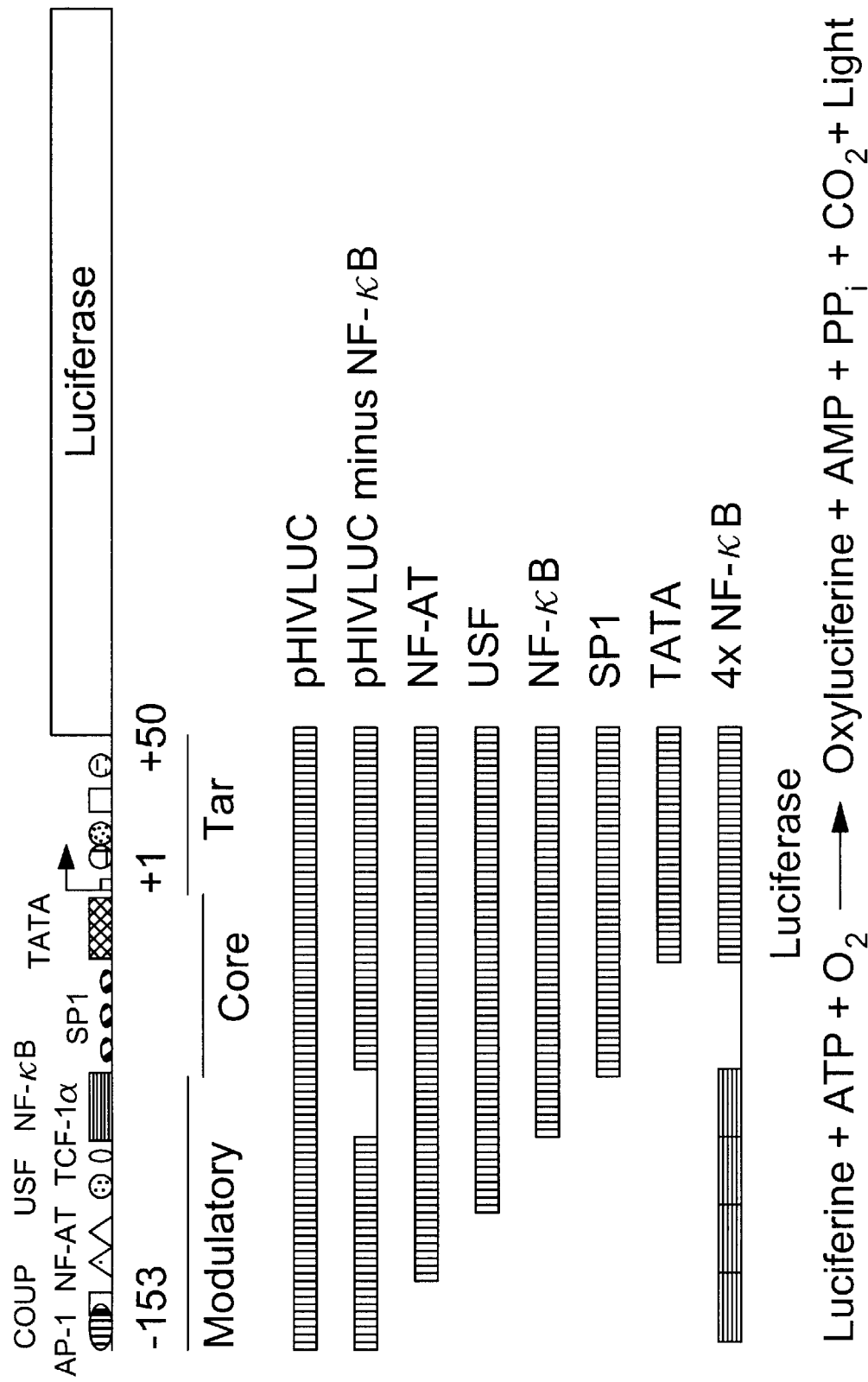
FIG. 1: Plasmids that are used for studies on the effect of compounds on HIV promotor activity.

3.d. HIV-LTR Driven Luciferase Gene Expression to Study the Effect on HIV Promoter Activity pHIV-CAT constructs are obtained from the NIH AIDS Research and Reference Reagent Program (National Institute of Allergy and Infectious diseases, Rockville, Md., USA). The HIV-CAT plasmids contained HindIII and BamHI restriction sites flanking the CAT gene. The HIV-long terminal repeat (LTR) sequence is found upstream this gene. The CAT gene is excised out of the plasmid and the luciferase (LUC) gene contained in a pGL3-basic vector (provided by Promega, Madison, USA) is obtained after HindIII and BamHI digestion. The LUC gene is then ligated into the empty HIV vectors, yielding HIV-LUC plasmids, with LTR-driven luciferase activity. The basic plasmid that does not contain any binding sites for eukaryotic transcription factors is pCD54 which only contains the 3' HIV-1 LTR region containing the TATA box and the TAR (where to HIV-1 tat can bind) region downstream of the LUC gene. In addition, the following plasmids are available:

p3NF-kB wich contains 3 NF-kB binding sites downstream of pCD54; pCD52 which contains one binding site for SP1 downstream of pCD54; pCD23 which contains 3 SP1 binding sites and two NF-kB binding sites downstream of pCD54; pCD16 which contains one USF, one TCF-1a, two NF-kB, and three SP-1 binding sites downstream of pCD54; pCD7 which contains one NF-AT, one USF, one TCF-1a, two NF-kB, and three SP-1 binding sites downstream of pCD54; pHIV-LUC which contains the complete HIV-1 LTR region downstream of pCD54. The HIV-1 LTR consists of one AP-1 COUP, one NF-AT, one USF, one TCF-1a, two NF-kB, and three SP-1 binding sites. FIG. 1 shows the collection of plasmids that are available.

E.coli DH5aF' that are made competent with $CaCl_2$ and are subsequently transformed with the pHIV-LUC vector and the other plasmids that are described above. The plasmids are isolated from these transformants after overnight incubation. Cells ($5×10^6$ cells/ml) are transfected by electroporation with 1 mg of a plasmid expressing the LUC reporter gene, under the control of the HIV-LTR. In addition to this plasmid the cells are co-transfected with 1 mg tat plasmid as an extra transcription stimulus and 1 mg b-gal plasmid as control for transfection efficiency. After transfection, the cells are incubated at 37° C. for 2 hours in medium containing 10% FCS and 10 mg/ml gentamicin. The transfected cells are subsequently incubated with various concentrations of the drug under investigation and then stimulated by 20 ng/ml phorbol 12-myristate 13-acetate (for PBMC and PBL) or 10 mM N-acetyl-L-cysteine (for MDM). 16 hours after stimulation and compound incubation, firefly luciferase activity is measured employing the single-luciferase™ reporter assay system (Promega, Madison, USA). (β-galactosidase activity is measured 16 hours after stimulation and compound addition. The amount of activity correlates to the light emission measured by LUMAC Biocounter M2500 at 562 nm. Cells stimulated in the absence of the drug under investigation serve as control cells.

What is claimed is:

1. A method for treating a viral infection in a subject suffering therefrom, said method comprising administering to the subject a compound of the general formula:

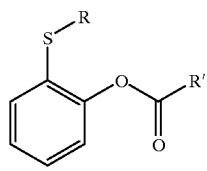

wherein

R is H, $CF_3$ or a C1–C10, branched or urbranched, substituted or unsubstituted saturated or (poly) unsaturated, (cyclo)alkyl, alkene, alkyne, (cyclo),aryl, aryl(cyclo)alkyl, (cyclo)alkylaryl, alkoxyaryl, alkoxyalkene, alkoxyalkyne, enyne, diene, diyne or alkoxyalkyl, and R' is selected from the group consisting of H, $CH_3$, $CF_3$, $CH_2Cl$ and $CH_2Br$, in a pharmaceutically acceptable manner in a pharmaceutically acceptable amount.

2. The method according to claim 1 wherein R is selected from the group consisting of H, $CH_3$, $CH_2CH_3$, $(CH_2)_2CH_3$, $(CH_2)_3CH_3$, $(CH_2)_4CH_3$, $(CH_2)_5CH_3$, $(CH_2)_6CH_3$, $CH(CH_3)_2$, $C(CH_3)_3$, $CH=C=CH_2$, $(CH_2)_2O(CH_2)_3CH_3$, $CH_2HC=CH(CH_2)_3CH_3$, $CH_2C\equiv C(CH_2)_3CH_3$, $CCH_2C\equiv C(CH_2)_2CH_3$, $CH_2C\equiv C-CH_2CH_3$, $CH_2C\equiv C-CH_3$, $CH_2C\equiv CH$ and isomers or homologues thereof.

3. The method according to claim 1 wherein said viral infection is a retroviral infection.

4. The method according to claim 3 wherein said retroviral infection is caused by a immunodeficiency virus.

5. The method according to claim 3 wherein said treatment additionally comprises administering another pharmaceutical composition.

6. The method according to claim 5 said other pharmaceutical composition comprises at least one antiviral agent.

7. The method according to claim 5 wherein said treatment additionally comprises treatment of inflammatory responses suffered by said subject.

* * * * *

UNITED STATES PATENT AND TRADEMARK OFFICE
CERTIFICATE OF CORRECTION

PATENT NO.     : 6,387,959 B1                                                Page 1 of 1
DATED          : May 14, 2002
INVENTOR(S)    : Johannes Servatius Leornardus Maria Nottet It is certified that error appears in the above-identified patent and that said Letters Patent is hereby corrected as shown below:

<u>Column 9,</u>
Line 20, change "ANY." to -- NY --

<u>Column 13,</u>
Line 24, change "urbranched" to -- unbranched --

Signed and Sealed this

Twenty-fifth Day of March, 2003

JAMES E. ROGAN
*Director of the United States Patent and Trademark Office*